United States Patent [19] [11] 4,140,719
Tull et al. [45] Feb. 20, 1979

[54] SOLID-LIQUID PHASE TRANSFER CATALYSIS IMPROVED METHOD OF PREPARING 2,4-DIFLUOROANILINE

[75] Inventors: Roger J. Tull, Metuchen; Leonard M. Weinstock, Bellemead; Ichiro Shinkai, Westfield, all of N.J.

[73] Assignee: Merck & Co., Inc., Rahway, N.J.

[21] Appl. No.: 847,186

[22] Filed: Oct. 31, 1977

[51] Int. Cl.$^2$ .................... C07C 85/11; C07C 85/24; C07C 79/12
[52] U.S. Cl. .................................. 260/580; 260/440; 260/446; 260/447; 260/567.6 M; 260/606.5 F; 260/646
[58] Field of Search ............... 260/580, 646, 576.6 M, 260/440, 446, 447, 606.5 F

[56] References Cited
U.S. PATENT DOCUMENTS

| 2,634,280 | 4/1953 | Tribalat et al. ................ 260/440 X |
| 3,024,283 | 3/1962 | Metcalfe et al. ............. 260/567.6 M |
| 3,117,983 | 1/1964 | Matthews ........................ 260/440 X |
| 3,721,706 | 3/1973 | Hoffmann et al. ....... 260/567.6 M X |
| 3,992,432 | 11/1976 | Napier et al. ................... 260/465.1 |

FOREIGN PATENT DOCUMENTS 960046 6/1964 United Kingdom .................... 260/580

OTHER PUBLICATIONS

Finger et al., "JACS", vol. 78, pp. 6034–6037 (1956).
Kraus et al., "Catal. Proc. Int. Congr.", 5th, pp. 1073–1084 (1972).

Primary Examiner—Winston A. Douglas
Assistant Examiner—John Doll
Attorney, Agent, or Firm—Raymond M. Speer; Mario A. Monaco

[57] ABSTRACT

A method of preparing 2,4-difluoroaniline by reacting 2,4,5-trichloronitrobenzene with a fluorinating agent in the presence of a solid-liquid phase interface, and utilizing a phase transfer catalyst to form 2,4-difluoro-5-chloronitrobenzene, followed by hydrogenation with hydrogen in the presence of a hydrogenation catalyst to form 2,4-difluoroaniline.

10 Claims, No Drawings

SOLID-LIQUID PHASE TRANSFER CATALYSIS IMPROVED METHOD OF PREPARING 2,4-DIFLUOROANILINE

BACKGROUND OF THE INVENTION (1) Field of the Invention

A method of preparing 2,4-difluoroaniline.

(2) Description of the Prior Art

G. C. Finger and C. W. Kruse, in JACS, 78, 6034 (1956), have described fluorination of 2,3,4-trichloro nitrobenzene with potassium fluoride in dimethylsulfoxide, to form 1,3-difluoro-2-chloro-6-nitrobenzene, but in low yield. Finger et al., in JACS, 81, 94 (1959), have described fluorination of 3,4,5-trichloronitro-benzene with potassium fluoride in dimethylformamide, to form 3,5-dichloro-4-fluoronitrobenzene in fairly high yield. However, the art does not suggest the specific fluorination by chlorine replacement to form 2,4-difluoro-5-chloronitrobenzene achieved with the method of the present invention, nor the high yield efficiency achieved with phase transfer catalysis in said method.

U.S. Pat. No. 3,992,432 describes a process for catalyzing heterogeneous ionic organic reactions in a system of multiple liquid phases in which the reactants are located in different phases. The catalysts are certain organic quaternary salts. However, the method of the patent is one involving only liquid phases, especially an organic phase and an aqueous phase, and there is no suggestion of employing a solid phase and a liquid phase as in the method of the present invention.

Christensen et al., in *Chem. Res.*, 74, 351 (1974), and Gokel and Durst, in *Aldrichimica Acta*, 9, 3 (1976), describe the use of crown ethers to catalyze a variety of synthetic reactions by complexing with an insoluble reagent, rendering the entire complex soluble in organic solvents. However, the crown ethers suffer from the disadvantages of limited solubility, cation specificity, and high cost; none of which characterize the phase transfer catalysts of the present invention.

Hydrogenolysis of various halobenzenes with hydrogen over palladium-carbon by M. Kraus and V. Bazant, reported in *Catal., Proc. Int. Congr.*, 5th, 1972, 2, 1073–84, determined that reactivity decrease occurred in the order Br, Cl, F. and R. E. Florin et al., in *J. Res. Natl. Bur. St.*, 62, 119 (1959) found that hydrogenation with hydrogen over palladium-carbon of 2,3,4,5-tetrafluorochlorobenzene formed 1,2,3,4-tetrafluorobenzene in fairly high yield. However, when catalytic reduction over palladium black of aromatic fluoro chloro nitro compounds was carried out by N. Vorozhtsov et al., reported in *Zhur. Obshchei Khim.*, 31, 1229-32 (1961), it was found that 2,4-difluoro-5-chloroaniline was formed. Thus, the art does not suggest the catalytic reduction of the method of the present invention whereby the nitro group is reduced to amine and the chlorine substituent is displaced without affecting the fluorine substituents, in a very specific manner.

A commonly employed method in the art currently for preparing 2,4-difluoroaniline is one which prepares 1,3-dichlorobenzene as an intermediate and uses benzene as a starting material. However, this process requires use of AlCl$_3$ catalyst, an expensive material, as well as fractional distillation. The intermediate is then nitrated, and fluorine replacement and reduction produces 2,4-difluoroaniline. The reactions of this conventional method may be illustrated as follows:

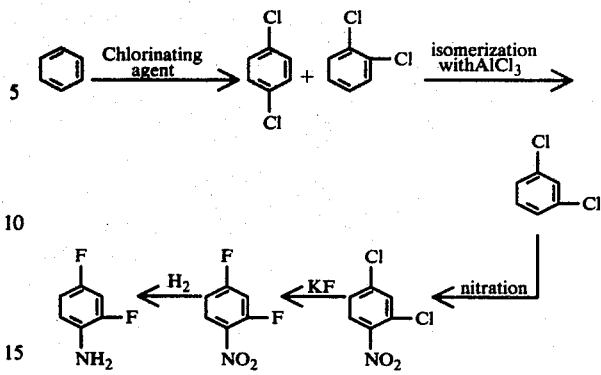

The method of the present invention avoids the expensive isomerization step of the above process by employing trichlorobenzene, as inexpensive starting material, with specific chlorine removal at the time of fluorine replacement.

SUMMARY OF THE INVENTION

The method of the present invention is concerned with preparation of 2,4-difluoroaniline.

The present invention is particularly concerned with a fluorination replacement reaction which employs a solid-liquid phase transfer catalyst to achieve high yields. In that regard it comprises an unexpected improvement in the method of preparing 2,4-difluoroaniline disclosed in our copending application Ser. No. 847,187, filed Oct. 31, 1977.

More particularly, the method of the present invention comprises two steps characterized by high specificity whereby preparation of 2,4-difluoroaniline is greatly simplified and improved. The first step involves fluorination of 2,4,5-trichloronitrobenzene whereby two of the chlorine substituents are replaced by fluorine in a specific manner to form 2,4-difluoro-5-chloronitrobenzene. This first step is carried out with greatly improved efficiency and high yields through the use of a quaternary compound solid-liquid phase transfer catalyst in the presence of a solid-liquid phase interface. The second step involves hydrogenation of the 2,4-difluoro-5-chloronitrobenzene whereby the nitro substituent is reduced to amine, the chlorine substituent is displaced to form HCl, and the two fluorine substituents remain unaffected. The hydrogenation step is, thus, quite specific.

The method of the present invention, comprising basically two steps, but three separate reactions, may be schematically represented as follows:

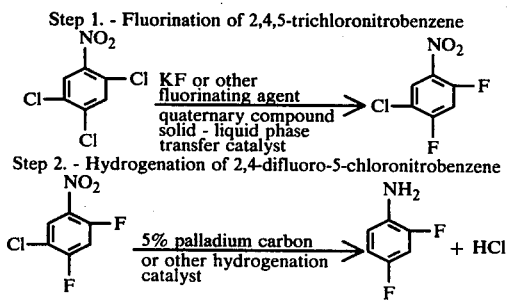

The starting material for the method of the present invention may be 1,2,4-trichlorobenzene, an inexpensive material. This material must then be nitrated to prepare 2,4,5-trichloronitrobenzene. However, it is preferred to employ 2,4,5-trichloronitrobenzene as a starting material since it is fairly readily available and relatively inexpensive.

The fluorination step of the method of the present invention, in addition to employing a quaternary compound solid-liquid phase transfer catalyst, is carried out under essentially anhydrous conditions using a fluorinating agent selected from the group consisting of NaF, KF, CsF, and $C_{1-4}$ alkyl quaternary ammonium fluoride, and mixtures thereof. KF is preferred as the fluorinating agent. Since the presence of water slows the fluorination considerably, the reaction conditions must be substantially anhydrous, although trace amounts of water can be tolerated. Anhydrous conditions are usually maintained by employing an organic solvent reaction medium. Basically any organic solvent medium which will dissolve the 2,4,5-trichloronitrobenzene and in which the fluorinating agent is essentially insoluble, may be employed. Hydrocarbon solvents are preferred, especially aromatic hydrocarbons, unsubstituted and substituted with groups independently selected from lower alkyl and halogen, for example, benzene, toluene, xylene, chlorobenzene, o-dichlorobenzene and trifluorobenzene. The solvent reaction medium may also comprise a dipolar and aprotic solvent. A number of such solvents are suitable for example, one selected from dimethylsulfoxide, tetramethylsulfone, dimethylformamide, dimethylacetamide, tetramethylurea, dimethylsulfone, and hexamethylphosphoramide. A molar excess of the fluorinating agent, e.g., potassium fluoride, is used, usually of at least five-fold in amount. The fluorination reaction is carried out at elevated temperatures of from about 75° to about 225° C., preferably of from about 100° to about 175° C., and for a period of time ranging from about 3 to about 30 hours, usually from 8 to about 20 hours.

As already mentioned above, the unexpected improvement of the present invention comprises use of a quaternary compound solid-liquid phase transfer catalyst during the fluorination step. Accordingly, the reactants for the fluorination step are carried in two separate phases. The solid fluorinating agent, for example KF, is one phase, a solid phase, and the other phase is a liquid phase and comprises the reactant 2,4,5-trichloronitrobenzene dissolved in an organic solvent in which the solid fluorinating agent is insoluble or only slightly soluble, for example toluene. Two discrete phases thus exist in which the reactants of the fluorination step are separately carried. It is also possible to employ as the liquid phase, the 2,4,5-trichloronitrobenzene reactant itself, in a molten state. The low melting point of this normally solid material makes such a procedure fairly easy to accomplish and, further, dispenses with the need for an organic solvent medium. In this case, the two phases, solid and liquid, would consist of the two reactants themselves, that is, 2,4,5-trichloronitrobenzene and KF, for example.

The solid-liquid phase transfer catalysis occurs essentially by a mechanism of transfer across the phase interface in which the ionic functional group of the fluorinating agent, that is, the $F^\ominus$ ion, is transferred from the solid phase to the liquid phase containing the reactant 2,4,5-trichloronitrobenzene. The quaternary compound solid-liquid phase transfer catalyst acts as an acceptor for the ionic functional group from the solid phase, and as a donor of that ionic functional group to the liquid phase. Thus, the quaternary compound acts as a transporting medium or element for the ionic functional group, the $F^\ominus$ ion.

The quaternary compounds employed as solid-liquid phase transfer catalysts in the fluorination step of the method of the present invention may be represented by the formula

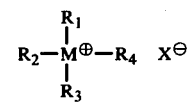

where M is selected from nitrogen, arsenic, phosphorus, antimony and bismuth; $X^\ominus$ is any anion capable of dissociating from the cation $M^\oplus$, and is preferably halide; and $R_1$, $R_2$, $R_3$ and $R_4$ are monovalent hydrocarbon radicals selected from alkyl, alkenyl, alkynyl, aryl, alkaryl, aralkyl, and cycloalkyl.

The quaternary compound must be soluble in the liquid phase, that is, the organic solvent medium in which the 2,4,5-trichloronitrobenzene is dissolved or the 2,4,5-trichloronitrobenzene itself. For example, the quaternary compound must be soluble in toluene, the preferred solvent medium for the liquid phase. Accordingly, $R_1$, $R_2$, $R_3$ and $R_4$ must be selected so that the total number of carbon atoms involved is at least 18, and preferably higher. While some maximum number of total carbon atoms necessarily exists, that number is not generally significant, and, as a practical matter, the maximum number of carbon atoms involved should not be greater than about 60.

While it is preferred to employ a single quaternary compound as the solid-liquid phase transfer catalyst, it is possible to employ mixtures of the quaternary compounds in this way.

Examples of quaternary compounds which may be employed as transfer catalysts in the fluorination step of the method of the present invention are the following:

trioctylethylammonium bromide
tridecylmethylammonium chloride
didodecyldimethylammonium chloride
tetraheptylammonium iodide
dioctadecyldimethylammonium chloride
tridecylbenzylammonium chloride
triphenyldecylphosphonium iodide
tributylhexadecylphosphonium iodide
tribenzyldecylarsonium chloride It is also possible to employ quaternary compounds in which one or more of $R_1$, $R_2$, $R_3$ and $R_4$ are mixtures of long chain alkyl groups within a specified range. Thus, in a preferred quaternary compound, Aliquat 336 available from Mc Kerson Corp., Minneapolis, Minnesota 55408, one R group is methyl while the remaining R groups are various long chain alkyl groups in the range of eight to twelve carbon atoms, and the compound may be represented by the formula: $(n-C_8-C_{12})_3NCH_3^\oplus Cl^\ominus$. The compound has an average molecular weight of about 500.

All of the above quaternary compounds are generally satisfactory for use in the method of the present invention, and will usually be, as they must, inert or non-reactive with respect to the various materials employed in the reaction mixture, except the reactants themselves.

The amount of quaternary compound which it is necessary to employ will vary, depending, among other things, upon the solvent medium which is selected and the desired rate of reaction. Generally, however, the amount employed will usually be from about 10 to about 75 weight percent, based on weight of 2,4,5-trichloronitrobenzene in the solvent medium of the liquid phase.

The 2,4-difluoro-5-chloronitrobenzene formed by the fluorination step described above is next subjected to the catalytic hydrogenation step of the method of the present invention. The hydrogenation catalyst employed is preferably a 5% palladium carbon catalyst. This catalyst is an activated carbon substrate impregnated with 5% by weight of palladium. The manner of impregnation is not critical and palladium carbon catalysts prepared by various conventional processes are suitable. A 5% palladium carbon catalyst available from Engelhard Industries, Inc. has been found especially suitable. A 10% palladium carbon catalyst has been found to give results essentially similar to those obtained with the 5% palladium catalyst. Other hydrogenation catalysts which may be employed are $Ni/Cr_2O_3$ or Raney nickel catalysts, preferably on an activated carbon substrate. The amount of catalyst employed will usually be from about 5% to about 25% by weight of the amount of 2,4-difluoro-5-chloronitrobenzene starting material. The catalyst material and starting material are added to a suitable solvent, for example, methanol or higher alkanol, or aqueous mixtures of these together with sodium acetate or other mild base to neutralize the HCl formed during the reaction. Hydrogen is then bubbled through the reaction solution by means of suitable apparatus, for example, a Parr hydrogenater. The reaction solution is stirred or shaken while hydrogen is passed through the solution.

The reaction solution is initially maintained at a temperature of from about 0° to about 100° C. However, reduction of the nitro group is exothermic and cooling may be required if the apparatus employed does not permit dissipation of the heat generated. Otherwise, by starting at a sufficiently low temperature, it is possible to run the total hydrogenation process straight through without addition or extraction of any heat. The chlorine removal portion of the hydrogenation process requires temperatures between about 20° to 100° C. Thus, it is possible, but not necessary, to carry out the hydrogenation process in essentially to stages: nitro group reduction followed by chlorine removal.

The hydrogen pressure during hydrogenation is usually maintained between about 3 and 10 atmospheres, most usually about 3 atmospheres or 40 psig. Stoichiometrially, four moles of hydrogen are required for hydrogenation of 2,4-difluoro-5-chloronitrobenzene. As a practical matter, hydrogen is passed through the reaction solution until the reaction is complete, since all the hydrogen which is required for the hydrogenation reaction will be consumed, and any excess or additional amounts will have no adverse consequences. Thus, the time required for the hydrogenation step will depend on a number of factors, including hydrogen pressure and temperature of the reaction solution. Usually, hydrogenation will be complete in from about 1 to about 5 hours.

Typically, the hydrogenation may be carried out as follows: after at least about three moles of hydrogen have been passed through the solution, the solution is heated to a temperature of from 50° to 70° C. and an additional at least two moles of hydrogen are passed through the solution.

EXAMPLE 1

Preparation of 2,4-difluoro-5-chloronitrobenzene:

Fluorination of 2,4,5-trichloronitrobenzene 5.0g. ($2.208 \times 10^{-2}$ mole) of 2,4,5-trichloronitrobenzene, 2.8g ($4.82 \times 10^{-2}$ mole) of anhydrous potassium fluoride, 50 ml. of dimethylsulfoxide, and 3.0g. (0.006 mole) of Aliquat 336, a tetra-alkyl ammonium chloride, were admixed together and heated at 100° C. for 1 hr., and at 120° C. for 3 hrs. The mixture was then poured into 100 ml. of hot water and the reaction product was separated by steam distillation. The 2.6 liters of distillate was then extracted with 80 ml. of ether for each of a total of six times. The extract was dried over $Na_2SO_4$ to give 3.01 g. of a crude, pale yellow oil, a yield of 70.5%. Results were confirmed by thin layer chromatography and gas chromatography, which indicated the final product to be 78.2% 2,4-difluoro-5-chloronitrobenzene.

EXAMPLE 2

Preparation of 2,4-difluoro-5-chloronitrobenzene:

Fluorination of 2,4,5-trichloronitrobenzene 5.0g. ($2.208 \times 10^{-2}$ mole) of 2,4,5-trichloronitrobenzene, 2.8g. ($4.82 \times 10^{-2}$ mole) of anhydrous potassium fluoride, 50 ml. of dimethylsulfoxide, and 3.0g. (0.006 mole) of Aliquat 336, a tetra-alkyl ammonium chloride, were admixed together and heated at 90°–100° C. for 17 hours. The reaction mixture was then poured into 20 ml. of water and the reaction product was separated by steam distillation. Approximately 2 liters of distillate was extracted twice with 200 ml. of ether for each extraction. The combined extract was dried to give a crude oil. The yield of final product was 2.98g. or 69.7%. Results were confirmed by thin layer and gas chromatography for 2,4-difluoro-5-chloronitrobenzene.

EXAMPLE 3

Preparation of 2,4-difluoro-5-chloronitrobenzene:

Fluorination of 2,4,5-trichloronitrobenzene 5.0g. ($2.208 \times 10^{-2}$ mole) of 2,4,5-trichloronitrobenzene, 2.8g. ($4.82 \times 10^{-2}$ mole) of anhydrous potassium fluoride, 50 ml. of toluene, and 3.0 g. (0.006 mole) of Aliquat 336, a tetra-alkyl ammonium chloride, were admixed together and heated at 90°–95° C. for 17 hours. The mixture was then maintained at 100°–105° C. for 8 hours, after which it was boiled under reflux for 16 hours. Then, 560 mg. of additional anhydrous potassium fluoride was added and the mixture was boiled under reflux for 23 hours. The reaction product was next separated by steam distillation. Two liters of distillate was extracted with ether and the extract dried to give a crude, yellow to orange, oil. The yield of final product was 3.96g. or 92.7%. Gas chromatographic analysis indicated that the final product contained 81.6% of 2,4-difluro-5-chloronitrobenzene.

EXAMPLE 4

Preparation of 2,4-difluoro-5-chloronitrobenzene:

Fluorination of 2,4,5-trichloronitrobenzene 20g. ($8.83 \times 10^{-2}$ mole) of 2,4,5-trichloronitrobenzene was dissolved in 25 ml. of toluene. Next, 13.0 g. ($2.24 \times 10^{-1}$ mole) of potassium fluoride was first dried overnight at 80° C. under vacuum, and then added to 75 ml. of toluene with which it was azetropically distilled for 1 hour. Then, 4.0g. ($8 \times 10^{-3}$ mole) of Aliquat 336, a tetra-alkyl ammonium chloride, was added to 20 ml. of toluene and this solution was added to the potassium fluoride and toluene mixture and the total mixture was azeotropically distilled for 1 hour. The toluene solution of 2,4,5-trichloronitrobenzene was then slowly added to this total mixture. The reaction mixture was then refluxed for 119 hours, after which 15 g. of dimethylsulfoxide was added and the reaction mixture refluxed for 9 hours. The reaction mixture was then poured into 150 ml. of a saturated NaCl solution, and the reaction product was separated by steam distillation to give a crude, orange oil. Yield of final product was 15.1 g. or 88.4%. The final product was then distilled under vacuum to give a pale yellow liquid having a boiling point of 70°-72° C. The yield of this final product was 14.8g. or 86.6%.

EXAMPLE 5

Preparation fo 2,4-difluoro-5-chloronitroaniline:

Fluorination of 2,4,5-trichloronitrobenzene

A mixture of 20g. ($8.83 \times 10^{-2}$ mole) of 2,4,5-trichloronitrobenzene, 13g. ($2.24 \times 10^{-1}$ mole) of anhydrous potassium fluoride, and Aliquat 336 (4.0g., $8 \times 10^{-3}$ mole) in 75 ml. of dimethylsulfoxide was heated at 95°-100° C. for 23 hours. The reaction product was next separated by steam distillation yielding 2 liters of distillate. The distillate was extracted with dichloromethane four times using 70 ml. for each extraction; washed with water, then 5% sodium hydroxide, and again water; and then dried over sodium sulfate. Evaporation of the solvent gave 16.85 g. of crude 2,4-difluoro-5-chloronitrobenzene, a yield of 98.6%. Gas chromatography indicated a purity of 91%.

EXAMPLE 6

Preparation of 2,4-difluoroaniline:

Hydrogenation of 2,4-difluoro-5-chloronitrobenzene 2.0g. ($1.03 \times 10^{-2}$ mole) of 2,4-difluoro-5-chloronitrobenzene, together with 900 mg. ($1.1 \times 10^{-2}$ mole) of sodium acetate, and 0.2g. of 5% palladium carbon catalyst, was added to 30 ml. of methanol. 40 lbs of hydrogen was passed through the reaction mixture for 3 hours, after which it was heated to 60° C. During the following 6 hours and 14 minutes an additional 12 lbs of hydrogen was passed through the reaction mixture. The catalyst and sodium acetate were then removed by filtration and washed with 10 ml. of methanol. The reaction mixture was then concentrated to about 5 ml. and poured into 40 ml. of a 5% Na$_2$CO$_3$ solution. The solution was extracted with chloroform three times at 20 ml. per extract. The extract was dried over Na$_2$SO$_4$. The solvent was evaporated under reduced pressue and the residue was purified by vacuum distillation. The yield of final product was 640 mg., which was 48%.

EXAMPLE 7

Preparation of 2,4-difluoroaniline:

Hydrogenation of 2,4-difluoro-5-chloronitrobenzene

A solution of 2,6-difluoro-5-chloronitrobenzene (2.0g., $1.03 \times 10^{-2}$ mole) and triethylamine (2.1g., $2.06 \times 10^{-2}$ mole) was hydrogenated over 10% palladium carbon catalyst for 18 minutes at room temperature and for an additional 4 hours at 60° C. The catalyst was removed by filtration and washed twice with methanol, using 16 ml. of each wash. The solvent was evaporated and the residue was treated with dichloromethane. The resulting mixture was washed with 15 ml. of water, 70 ml. of ammonium hydroxide solution and then 15 ml. of water, and dried over Na$_2$SO$_4$. Evaporation of the remaining solvent gave 1.25 g. of a yellow oil, a yield of 94%. Gas chromatography established the reaction product to contain 89.5% 2,4-difluoro-aniline.

The 2,4-difluoroaniline prepared by the method of the present invention is a well known starting material and intermediate for a number of organic syntheses. See *The Merck Index*, ninth edition, pg. 415 (1976). Especially, the 2,4-difluoroaniline prepared by the method of the present invention is a useful starting material for preparation of 2',4'-difluoro-4-hydroxy-[1,1'-biphenyl]-3-carboxylic acid, a valuable anti-inflammatory and analgesic agent for therapeutic use.

What is claimed is:

1. A method of preparing 2,4-difluoroaniline comprising the steps of
    (a) fluorinating 2,4,5-trichloronitrobenzene in a solid-liquid phase system, under anhydrous conditions, wherein the solid phase comprises a fluorinating agent selected from NaF, KF, CsF, C$_{1-4}$ alkyl quaternary ammonium fluoride, and mixtures thereof; and the liquid phase comprises an organic solvent in which the 2,4,5-trichloronitrobenzene is soluble and in which the fluorinating agent is essentially insoluble; and the fluorination is carried out in the presence of one or more quaternary compound solid-liquid phase transfer catalysts of the formula

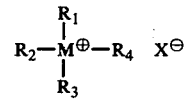

where M is nitrogen, arsenic, phosphorus, antimony, or bismuth; X$^\ominus$ is an anion capable of dissociating from the M$^\oplus$ cation; and R$_1$, R$_2$, R$_3$ and R$_4$ are monovalent hydrocarbon radicals selected from alkyl, alkenyl, alkynyl, aryl, aralkyl, alkaryl, and cycloalkyl, which together have a total of at least 18 carbon atoms; to form 2,4-difluoro-5-chloronitrobenzene; and
    (b) hydrogenating the 2,4-difluoro-5-chloronitrobenzene with hydrogen in the presence of a hydrogenation catalyst to form 2,4-difluoroaniline.

2. The method of claim 1 wherein the organic solvent is a dipolar, aprotic solvent.

3. The method of claim 2 wherein the dipolar, aprotic solvent is selected from dimethylsulfoxide, tetramethylsulfone, dimethylformamide, dimethylacetamide, tetramethylurea, dimethylsulfone, and hexamethylphosphoramide.

4. The method of claim 1 wherein the organic solvent is a hydrocarbon solvent.

5. The method of claim 4 wherein the hydrocarbon solvent is selected from aromatic hydrocarbons, unsubstituted and substituted with groups independently selected from lower alkyl and halogen.

6. The method of claim 5 wherein the hydrocarbon solvent is toluene.

7. The method of claim 1 wherein the fluorinating agent is KF.

8. The method of claim 1 wherein the quaternary compound is (n-C$_8$-C$_{12}$)$_3$NCH$_3^\oplus$Cl$^\ominus$.

9. The method of claim 1 wherein the hydrogenation catalyst is palladium impregnated activated carbon.

10. A method of preparing 2,4-difluoro-5-chloronitrobenzene comprising the step of fluorinating 2,4,5-trichloronitrobenzene in a solid-liquid phase system, under anhydrous conditions, wherein the solid phase comprises a fluorinating agent selected from NaF, KF, CsF, $C_{1-4}$ alkyl quaternary ammonium fluoride, and mixtures thereof; and the liquid phase comprises an organic solvent in which the 2,4,5-trichloronitrobenzene is soluble and in which the fluorinating agent is essentially insoluble; and the fluorination is carried out in the presence of one or more quaternary compound solid-liquid phase transfer catalysts of the formula:

$$R_2-\overset{R_1}{\underset{R_3}{M^{\oplus}}}-R_4 \quad X^{\ominus}$$

where M is nitrogen, arsenic, phosphorus, antimony, or bismuth; $X^{\ominus}$ is an anion capable of dissociating from the $M^{\oplus}$ cation; and $R_1$, $R_2$, $R_3$, and $R_4$ are monovalent hydrocarbon radicals selected from alkyl, alkenyl, alkynyl, aryl, aralkyl, alkaryl, and cycloalkyl, which together have a total of at least 18 carbon atoms; to form 2,4-difluoro-5-chloronitrobenzene.

* * * * *